United States Patent [19]

Richelsoph et al.

[11] Patent Number: 5,954,771
[45] Date of Patent: Sep. 21, 1999

[54] DUAL FIXATION PROSTHESIS

[75] Inventors: Marc Evan Richelsoph, Cordova; Kenneth William Russell, Bartlett, both of Tenn.; Roy Drake Bloebaum, Salt Lake City, Utah; Richard Edward Jones, Dallas, Tex.

[73] Assignee: Wright Medical Technology, Inc., Arlington, Tenn.

[21] Appl. No.: 08/017,568

[22] Filed: Feb. 16, 1993

[51] Int. Cl.⁶ .................................................. A61F 2/32
[52] U.S. Cl. ............................................. 623/23; 623/16
[58] Field of Search ................................ 623/16, 18, 22, 623/23

[56] References Cited

U.S. PATENT DOCUMENTS

| | | | |
|---|---|---|---|
| 4,983,183 | 1/1991 | Horowitz | 623/23 |
| 4,997,448 | 3/1991 | Filer | 623/23 |
| 5,047,061 | 9/1991 | Brown | 623/23 |
| 5,108,437 | 4/1992 | Kenna | 623/23 |
| 5,116,377 | 5/1992 | Skripitz et al. | 623/23 |
| 5,133,772 | 7/1992 | Hack et al. | 623/23 |
| 5,171,289 | 12/1992 | Torneir | 623/23 |
| 5,314,494 | 5/1994 | Huiskes et al. | 623/23 |

FOREIGN PATENT DOCUMENTS

| | | | |
|---|---|---|---|
| 0158534 | 10/1985 | European Pat. Off. | A61F 2/36 |
| 0393425 | 10/1990 | European Pat. Off. | |
| 0428127 | 5/1991 | European Pat. Off. | A61F 2/36 |
| 0444842 | 9/1991 | European Pat. Off. | A61F 2/46 |
| 9213218 | 11/1992 | Germany | A61F 2/36 |

OTHER PUBLICATIONS

D. O'Connor, D. Burke, R. Sedlacek, W. Harris, "Peak Cement Strains In Cemented Femoral Total Hip", 37th annual meeting, Orthopaedic Reasearch Society, Mar. 4–7, 1991, Anaheim, CA, p. 220.

J. Davies, G. Singer, W. Harris, "The Effect of a Thin Coating of Polymethylmethacrylate on the Torsional Fatigue Strength of the Cement–Metal Interface", Journal of Applied Biomaterials, vol. 3, 45–49 (1992).

M. Freeman, R. Tennant, "The Scientific Basis of Cement Versus Cementless Fixation", Clinical Orthopaedics & Related Research, No. 276, pp. 19–25 (1992).

*Primary Examiner*—Mickey Yu
*Attorney, Agent, or Firm*—Walker, McKenzie & Walker PC

[57] ABSTRACT

A long bone prosthesis (10) includes a neck portion (12), a stem portion (16) and an intermediate portion (20) disposed between the neck portion (12) and stem portion (16). The intermediate portion (20) includes seals for containing cement thereabout under pressure adjacent thereto and preventing leaking of cement therefrom during implantation of the prosthesis (10).

12 Claims, 5 Drawing Sheets

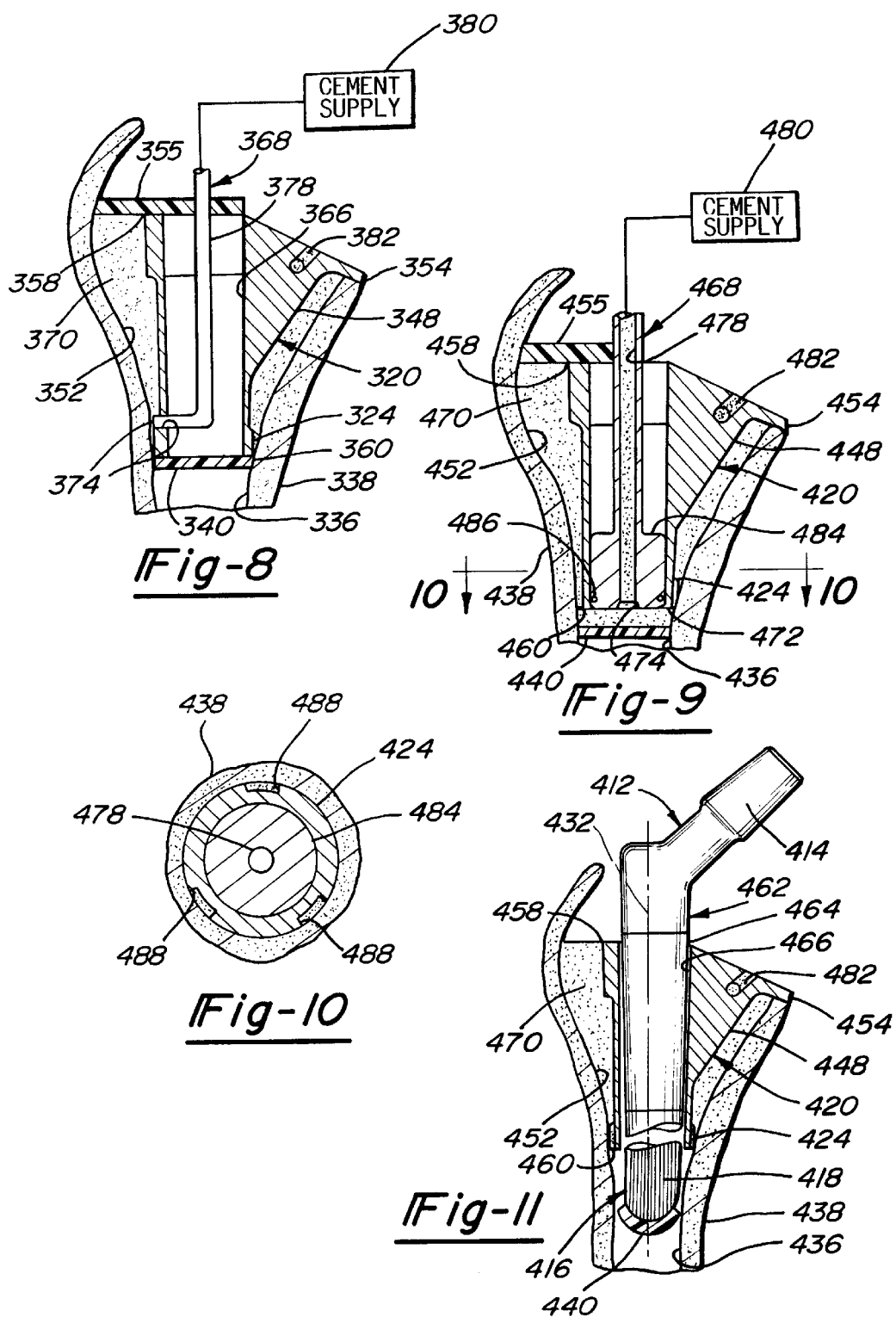

DUAL FIXATION PROSTHESIS

TECHNICAL FIELD

The present invention relates to a prosthesis for long bones and, more particularly to means for fixing such prosthesis in place.

BACKGROUND OF THE INVENTION

There are two accepted methods of fixating long bone prosthesis during implantation. For example, with particular regard to hip stem implantation, such implants are either cemented or press-fit in place. Cementation of a hip stem has a distinct advantage of initial fixation. Press-fit stems, however, often provide for better stress distribution as well as easier revision.

Implanting a cemented hip prosthesis involves three general steps. First, the femoral canal is prepared by methods well known in the art. Second, a bone plug is introduced and cemented into the femoral canal. And last, the prosthesis is then inserted and held in place until the cement sets.

Although pressurization of the cement in the canal is achieved by forcing the cement into the canal and then inserting the prosthesis, the pressure is low. Since presently used bone cement does not adhere well to a metallic surface, state of the art techniques achieve attachment by interdigitating the cement with a roughed or machined stem surface and the rough internal bone and/or bone pores. Therefore the cement adheres mainly by mechanical means.

Some authors have stated that a cement precoat of the hip stem enhances bone strength when inserted into the cement introduced into the femur. Davies, Singer and Harris, *The Effect of a Thin Coating of Polymethylmethacrylate on the Torsional Fatigue Strength of the Cement-Metal Interface,* Journal of Applied Biomateria, Vol. 3, 45–49 (1992). This is apparently correct since the cement precoat is applied under pressure and is therefore forced into the hip stem pores more completely and deeper than merely by inserting a hip stem into a cement bed in the femur. However, although this precoat technique may be better than standard cementing techniques, it can still have problems due to potential debonding or delaminating of the cement—cement interface. Therefore, it is ideal to gain the pressurization of the precoat but at the time of implantation so that the cement-prosthesis and cement-bone interfaces are achieved by one continuous cemented layer.

Although cemented hip stems are the state of the art standard by which other stems are measured in terms of implantation time, without the high risk of loosening of the stem, revisions of such stems are often quite difficult. Removing cement from the femoral canal below the lesser trochanter is often a long and involved procedure.

On the other hand, press-fit stems have advantages and disadvantages over cemented hip stems. Cement is relatively weak in tension and upon failure, debris from the broken cement mantel can cause a histiocytic response. The press-fit stem eliminates the cement mantel entirely. Secondly, strain distributions in the cement mantel at the distal tip may lead to premature distal cement failure and increased wear debris leading to osteolysis, as reported in "Peak Cement Strains in Cemented Femoral Total Hips". D. O'Conner, W. H. Harris et al. Orthopaedic Research Society, Vol. 16, Sec. 1, pg. 220. There is also often a lack of initial fixation in the press-fit hip implant.

SUMMARY OF THE INVENTION

In accordance with the present invention, there is provided a long bone prosthesis including a neck portion for simulating a long bone head and a stem portion including means for force fit engaging a long bone canal. An intermediate portion is disposed between the neck portion and the stem portion. The intermediate portion includes seal means disposed between the intermediate portion and each of the neck and stem portions for containing cement under pressure adjacent the intermediate portion and preventing leaking of cement therefrom during implantation of the prosthesis by contacting adjacent cortical bone as the stem is pressed into the long bone canal.

FIGURES IN THE DRAWINGS

Other advantages of the present invention will be readily appreciated as the same becomes better understood by reference to the following Detailed Description when considered in connection with the accompanying Drawings wherein:

FIG. 8 is a fragmentary cross-sectional view of yet another embodiment of the intermediate portion shown fixed within a proximal femur;

FIG. 9 is a cross-sectional view of still another embodiment of an intermediate portion of the present invention shown fixed within a proximal femur;

FIG. 10 is a cross-sectional view as taken along lines 10—10 of FIG. 9;

FIG. 11 is a fragmentary cross-sectional view of the prosthesis of FIG. 9 including an implanted stem and neck portion;

DETAILED DESCRIPTION OF THE INVENTION OF FIGS. 1–4

A long bone prosthesis constructed in accordance with the present invention is generally shown at 10 in the Figures. The preferred embodiment shown is for a hip stem implantation, although the present invention can be alternatively designed for implantation into other long bones of the leg or arm.

The prosthesis 10 generally includes three adjacent portions. A neck portion, generally shown at 12, is of the type for simulating the head of a long bone. In the embodiment shown in the Figures, the neck portion includes a taper 14 for force fit connection to a femoral head prosthesis. As well known in the art, such femoral head prostheses are impacted on the taper 14 of the neck portion 12. Other types of neck portions, well known in the art, can be utilized with the present invention.

Figure 1:
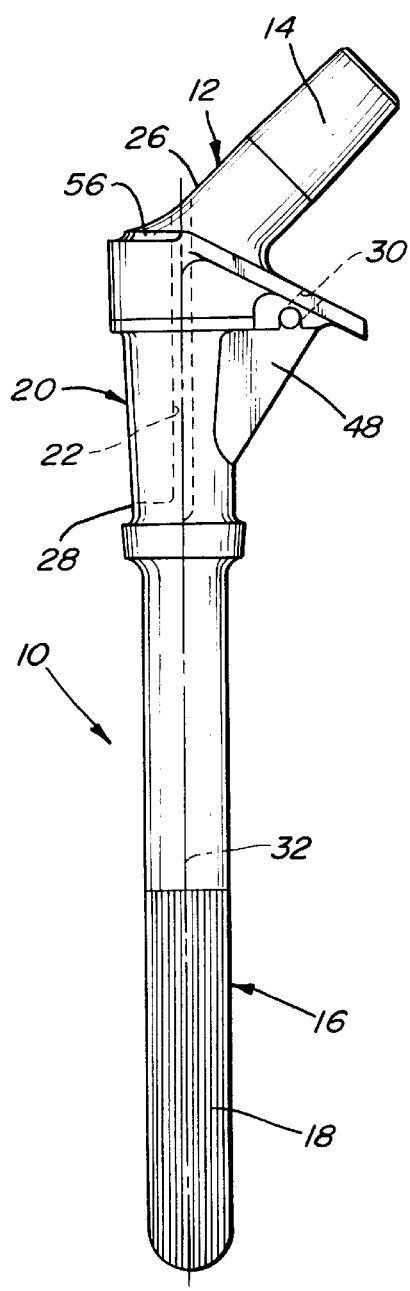
FIG. 1 is an elevational view of a hip prosthesis made in accordance with the present invention.

A stem portion, generally shown at 16 in FIG. 1, includes various means for force fit engagement into the long bone canal. Such means can take the form of flutes, spines, or both, for better initial fixation and torsional stability. The stem portion 16 in the Figures is shown to include flutes. The prosthesis includes an intermediate portion, generally shown at 20. The intermediate portion 20 is disposed between the neck portion 12 and the stem portion 16. Sealing mechanisms are disposed between the intermediate portion 20 and each of the neck and stem portions 14, 16, respectively, for containing cement under pressure adjacent the intermediate portion 20 and preventing leaking of cement therefrom during implantation of the prosthesis 10 by contacting adjacent cortical bone as the stem is press-fit into the long bone canal as described below.

That is, the invention provides a long bone prosthesis 10 including a first portion in the form of the stem portion 16 which is press-fit against an inner aspect of the cortical bone of the long bone and a second portion in the form of the intermediate portion 20 which is cemented to a different area of the inner aspect of the cortical bone of the long bone. Such a device includes the advantages of a prior art press-fit stem since it includes the advantageous strain distributions thereof while also including the advantages of the cemented stem implant.

Further, the present invention provides seal means which allow for high pressure cement injection thereby overcoming the problems of prior art cementing techniques which could not as effectively force the cement into the pores of the bone and prosthesis surface.

More specifically, referring to FIG. 1, the prosthesis 10 includes a first passageway 22 extending from the neck portion 12 and through the intermediate portion 20 adjacent to a first seal 24. That is, the passageway 22 includes a first opening 26 thereof extending through the neck portion 12 and a second opening 28 thereof extending through the intermediate portion 20 adjacent the first seal 24. In this manner, the second opening 28 is at the most distal portion of the intermediate portion, provided the prosthesis 10 is implanted in a proximal femur. This disposition of the passageway 22 allows for injection of cement through the passageway 22 to an area adjacent the intermediate portion 20, as explained below. A second passageway 30 extends between the neck portion 12 and the intermediate portion 20 adjacent to the neck portion 12 allowing for exit of blood and debris during injection of cement through the first passageway 22 as explained below.

Figure 3:
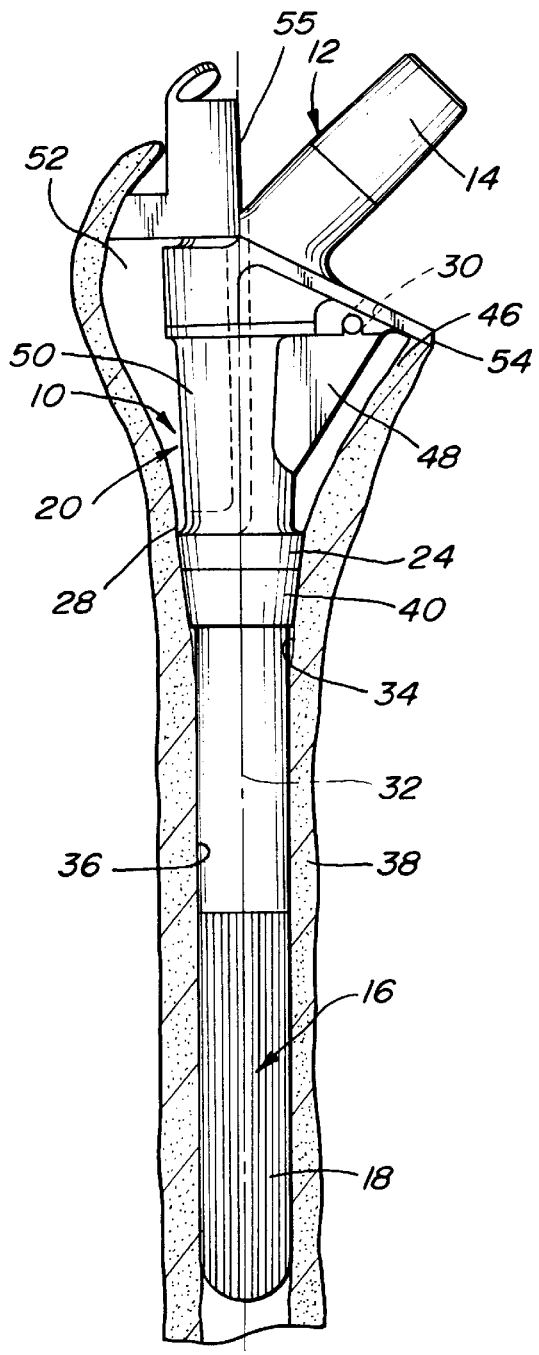
FIG. 3 is an elevational view partially in cross-section of the hip prosthesis press-fit into a femoral canal.

The prosthesis 10 includes a length thereof defining a longitudinal axis shown as broken line 32 in FIG. 1. The first seal 24 is disposed between the stem portion 16 and the intermediate portion 20 and extends radially outwardly from the longitudinal axis 32 for forcible, or press-fit seating at the mouth 34 of the canal of the long bone 38, as shown in FIG. 3. Preferably, the first seal 24 includes a conically-shaped outer surface, the surface tapering radially inwardly toward the stem 16. The first seal 24 is shown as an integral portion of the solid prosthesis member 10.

Figure 2:
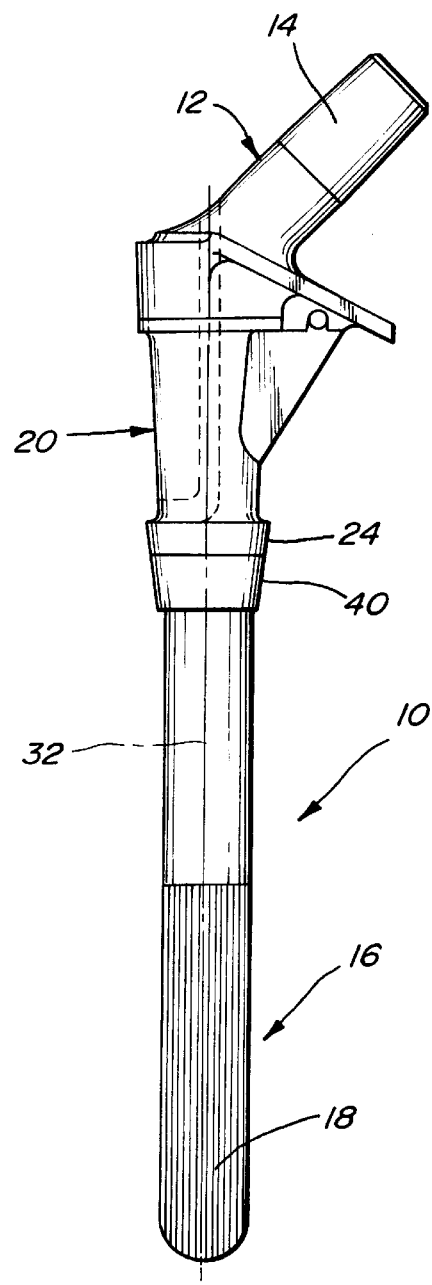
FIG. 2 is an elevational view of the hip prosthesis including an additional seal member.

As shown in FIGS. 2 and 3, a resilient seal member 40 being ring-shaped and preferably having an outer frusto-conical surface tapering distally toward the stem 16 is disposed subjacent to the first seal 24. The resilient seal member 40 can be an elastomer, polymer or bioresorbable material.

Figure 4:
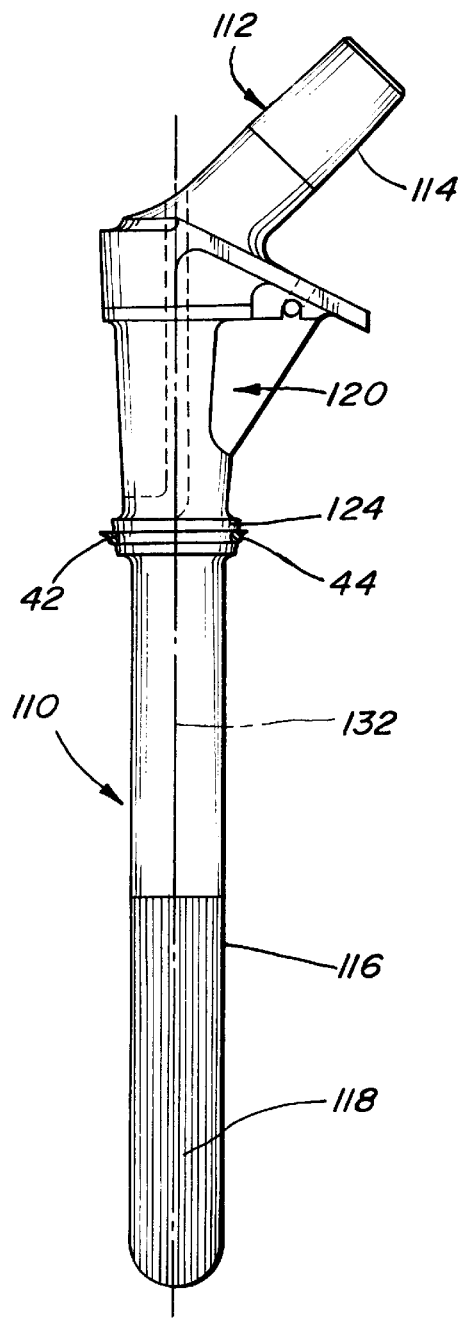
FIG. 4 is an elevational view of a second embodiment of the present invention.

As shown in the embodiment 110 in FIG. 4, wherein like portions of the prosthesis 110 are referenced with like numbers preceded by the numeral 1, the first seal 124 can include an annular recess 42 extending radially inwardly from the outer surface thereof. A ring-shaped resilient seal member 44 is disposed in the annular recess 42. The resilient seal 44 can be an elastomer, polymer, or bioresorbable ring or the like. The resilient seal in the form of seal member 40 (FIGS. 2 and 3) or seal member 44 (FIG. 4) cooperates with the first seal 24, 124 to perfect a seal between the stem portion 16, 116 and the mouth 34 of the long bone canal 36.

The prosthesis 10 includes a two-part second seal mechanism between the neck portion 12 and the intermediate portion 20 extending radially outwardly therefrom for sealing engagement with an inner cortical boundary 46 of the long bone 38, as shown in FIG. 3. More specifically, the intermediate region 20 includes an anti-rotation mechanism in the form of an anti-rotation lug 48 extending radially outwardly therefrom along a length of the longitudinal axis 32 and tapering inwardly and downwardly and spaced from the first seal 24 for mating engagement with the cortical bone to prevent relative rotation therebetween. As shown in FIG. 3, the intermediate portion 20 including the anti-rotation lug portion 46 and the central portion 50 of the intermediate portion 20 are recessed radially inwardly relative to the adjacent first 24 and second seals as well as recessed inwardly from an inner aspect of the cortical bone thereby forming a chamber 52 between the seals when the stem portion 16 is press-fit in the long bone canal 36.

The second seal mechanism includes a calcar collar portion 54 extending radially outwardly from the anti-rotation lug 48, adjacent to the neck portion 12, which enhances proximal loading characteristics as well as perfects a seal about that portion of the intermediate portion 20. That is, the calcar collar portion 54 defines a forward portion of the second seal opposed to a rear section of the second seal. The rear section of the second seal includes a resilient rear seal member 55 mounted on the intermediate portion 20 and extending radially outwardly therefrom for cooperating with the intermediate portion 20 to be fit between the intermediate portion 20 and the inner cortical boundary 46.

The rear section of the intermediate portion 20 includes a recessed seat portion 56, as shown in FIG. 1, for seating the resilient rear seal 55 thereon as shown in FIG. 3. The rear seal member 55 can be in the form of an inflatable resilient member for forming a pressure contact between the recessed seat portion 56 and the inner cortical boundary 46 when inflated and for being insertable and removable when deflated. Alternatively, the rear seal member 55 can be a resilient tubular member or a solid deformable elastomeric member for forming a press-fit contact between the recessed seat portion 56 and the inner cortical boundary 46.

The present invention further provides a method of fixating the long bone prosthesis 10, as for example into the femoral canal 36 as shown in FIG. 3. The method generally includes the steps of press-fitting the stem portion 16 of the prosthesis 10 into the canal 36 of the long bone 38 and then perfecting a seal of the boundaries of the intermediate portion 20 of the prosthesis 10 with the mouth 34 of the canal 36 adjacent the stem portion 16 of the prosthesis 10 and with the inner cortical boundary 46 adjacent the neck portion 12 of the prosthesis 10, the intermediate portion 20 being recessed from the cortical bone thereby defining the chamber 52 therebetween. Cement is injected under pressure between the seals and into the chamber 52 to cement the intermediate portion 20 of the prosthesis 10 to the cortical bone, thereby providing a combined press-fit and cement fixation.

More specifically, the initial implantation procedure that defines the press-fit portion of the implant is achieved by first press-fitting the seal member 40 onto the stem 16, as shown in FIG. 2, or about the first seal 124 as shown in FIG. 4. The hip stem 16 is then inserted into the prepared femoral canal 36. Preparation of a femoral canal 36 for stem 16 insertion requires techniques well known in the art. During the insertion, the first seal 24 contacts the cortical bone at the mouth 34 of the canal 36, as shown in FIG. 3. The stem 16 is press-fit into the canal 36 along with the bottom, or distal, portion of the first seal 24 and seal member 40. As discussed above, the stem 16 may include various means for enhancing initial fixation and torsional stability such as flutes, spines or other surface irregularities.

As shown in FIG. 3, the rear seal 55 is inflated about or press-fit onto the recessed seat portion 56 such that it combines with the collar portion 54 to perfect a seal about the intermediate portion 20 adjacent the neck portion 12 with the inner cortical boundary 46. This combined upper second seal of the intermediate portion 20 along with the lower first seal 24 isolate and enclose the chamber 52 in which the intermediate portion 20 is suspended. The collar portion 54 can also be cemented to the cortical bone during the initial press-fit procedure to provide for an even more efficient seal.

Fluidic uncured cement is injected through the injection port opening 26 via a tube (not shown), so that the cement fills the chamber 52 while pushing debris and blood out of the exit port 30. The cement pressurization can be measured by a pressure gauge (not shown) connected by a tube (also not shown) to the exit passageway 30. When cement filling is complete and an acceptable pressure is reached, the cement tubes connected to the injection port 26 and the exit passageway 30 are closed off until the cement sets. The rear seal member 55 and injection and exit tubes are then removed and the femoral head (not shown) is impacted on the taper 14.

The above method provides a prosthesis 10 which can be press-fit connected to a cortical bone while also being cemented to the cortical bone under pressure thereby achieving the advantages not previously achievable by either cement fixation or press-fit fixation techniques alone.

ALTERNATIVE EMBODIMENT OF FIGS. 5–13

Figure 5:
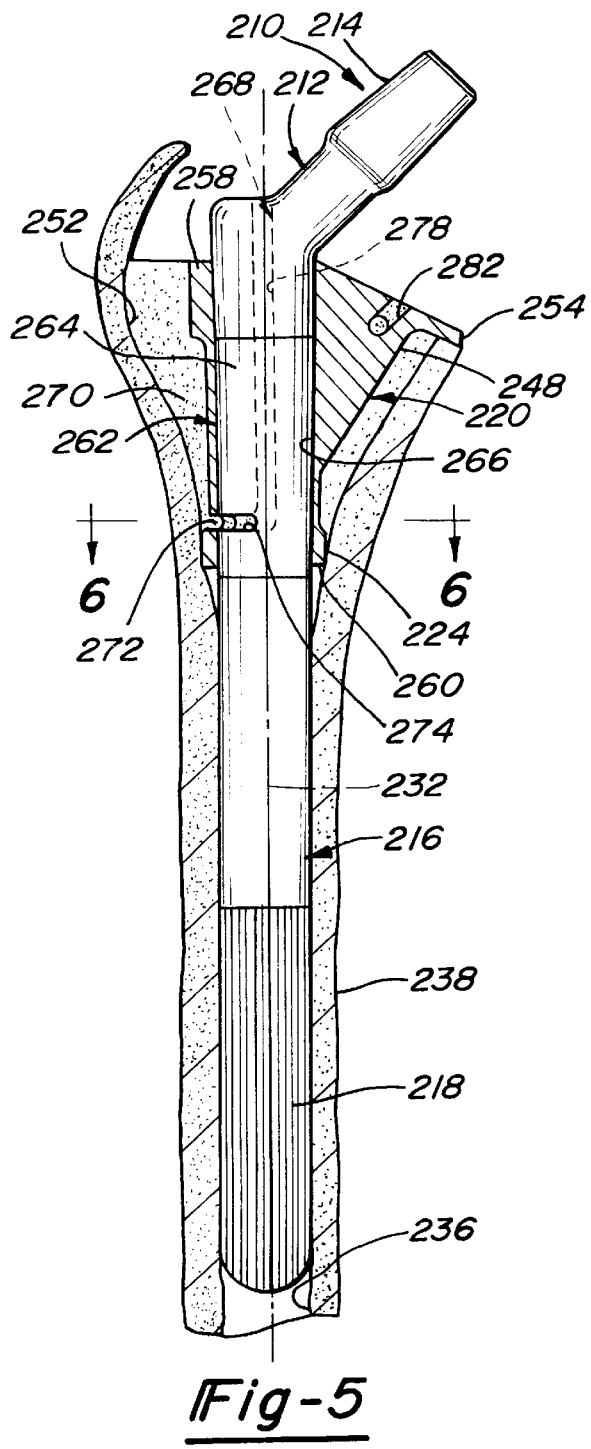
FIG. 5 is an elevational view of yet another embodiment of the present invention implanted within a femur, shown in cross-section.

According to an alternative embodiment of the invention as described above, a long bone prosthesis 210 is shown in FIG. 5, with the numerical suffix "2" designating corresponding reference characters to those like structural features described above. The prosthesis 210 includes a neck portion 212 having a taper 214 for force fit receiving a femoral head prosthesis (not shown). A stem portion 216 includes means 218 for force fit engaging a long bone canal 236. An intermediate portion 220 is disposed between the neck 212 and the stem 216 portions and has a proximal end 258 adjacent the neck portion 212 and a distal end 260 adjacent the stem portion 216. Seal means is disposed adjacent each of the proximal 258 and distal 260 ends of the intermediate portion 220.

A disconnection means, generally indicated at 262 in FIG. 5, is provided for disconnecting the intermediate portion 220 from each of the neck 212 and stem 216 portions prior to implantation, thus permitting individual and separate fixation of the stem 216 and intermediate portion 220. More specifically, the stem portion 216 and the neck portion 212 are integrally joined through an interposed shank 264. The intermediate portion 220 comprises an intermediate collar having a central passage 266 for receiving the shank 264. A fixation means is provided for fixedly connecting the shank 264 within the central passage 266. Preferably, and is best shown in FIGS. 5 and 11, the fixation means includes a mating frusto-conical frictional force fit connection between the shank 264 and the central passage 266. Thus, disconnection of the intermediate portion 220 from each of the neck 212 and stem 216 portions is effected by the modular nature of the intermediate portion 220 relative to the integral neck 212, shank 264 and stem 216 portions.

The intermediate portion 220 includes an anti-rotation lug 248 extending radially outwardly from the exterior surface of the intermediate collar 220.

Figure 6:
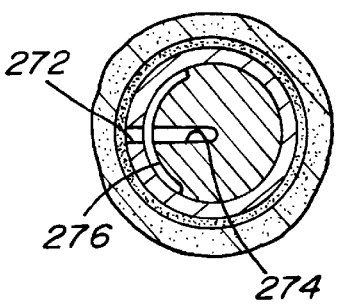
FIG. 6 is a cross-section as taken along lines 6—6 of FIG. 5.

The primary advantage of this alternative embodiment is that the intermediate portion 220 can be fixed in place in the prepared femoral canal independently of the stem portion 216 which, as described above, is preferably force fit within the prepared femoral canal 236. For this purpose, the seal means as described above is provided for containing cement under pressure about the exterior surface of the intermediate collar 220 and between the proximal 258 and distal 260 ends thereof. Cement injection means, generally indicated at 268 in FIGS. 5 and 6, is received into the central passage 266 for injecting fluidic cement 270 under pressure about the exterior surface of the intermediate collar 220 to fixedly retain the intermediate collar 220 in the prepared bone canal. More particularly, the cement injection means 268 has a peripheral engagement surface matingly engageable within the central passage 266, which in FIGS. 5–7 coincides with the frusto-conical shank 264.

Figure 7:
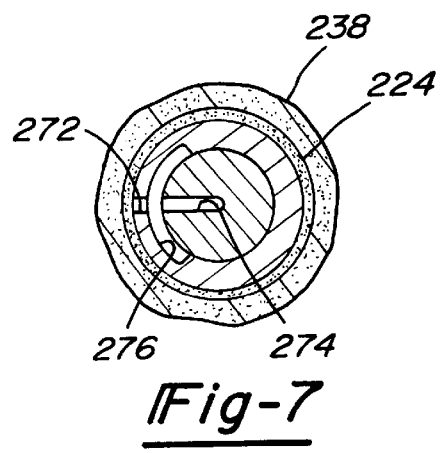
FIG. 7 is an alternative embodiment of the elongated groove shown in FIG. 6.

The intermediate collar 220 includes a cement flow opening 272 located adjacent the distal end 260 and communicable with an outlet 274 of the cement injection means 268. An elongated groove 276 is disposed between the cement flow opening 272 and the outlet 274 of the cement injection means 268. In the embodiment illustrated in FIG. 6, the elongated groove 276 is formed about a peripheral arcuate portion of the shank 264, whereas in FIG. 7 the elongated groove 276 is formed about an inner peripheral arcuate portion of the central passage 266. In each case, the elongated groove 276 permits for slight angular displacement between the outlet 274 from the cement injection means 268 and the cement flow opening 272. Thus, as shown in the embodiments of FIGS. 5–7, the cement injection means 268 includes a cement feed passage 278 extending through the shank 264 and communicating with the cement flow opening 272 to deliver fluidic uncured cement from a pump apparatus, schematically illustrated at 280 in FIGS. 8 and 9, to the exterior surface of the intermediate collar 220, to be trapped under pressure between the seal means located at the proximal 258 and distal 260 ends.

The seal means includes a calcar collar portion 254 in like fashion as that described above extending from the proximal end 258 of the intermediate collar 220 and interconnecting the anti-rotational lug 248. An exit port 282 extends through the calcar collar portion 254 for permitting egress of debris, blood, etc.

In FIG. 8, yet another embodiment of the modular intermediate collar portion 320 is shown wherein the cement injection means 368 includes a simple tube forming the cement feed passage 378 and disposed through a distal cement flow opening 372 formed through the central passage 366. The numerical suffix "3" hereinafter designates corresponding reference characters to those like structural features described above. In this embodiment, the integral neck and stem portions (not shown) are disassociated from the intermediate collar 320 during fixation of the intermediate collar 320. As shown, the seal means includes a first seal comprising the combined calcar collar portion 354 and a resilient, possibly inflatable, resilient seal member 355 to perfect a pressure-containing seal adjacent the proximal end 358 of the intermediate collar portion 320. Also, a second resilient seal member 340 is disposed contiguously subjacent the first seal 324 for preventing cement 370 migration into the prepared femoral canal 336. In the embodiment illustrated in FIG. 8, the resilient seal member 340 is a full disk-like member which, after cementation, must be removed through the central passage 366 prior to insertion of the stem portion. Alternatively, the resilient seal member 340 can be formed in annular fashion having an open center portion (not shown) aligned and substantially conforming with the central passage 366 such that a stem (not shown) is received directly through the central passage 366 and the open center of the resilient seal member 340. Thus, according to this alternative seal member 340 configuration, it is not required that the seal member 340 be removed after cementation.

FIGS. 9–11 illustrate yet another embodiment of the cement injection means 468 wherein the cement feed passage 278 is provided with an enlarged head 484 perfectly mating within the frusto-conical central passage 466 adjacent the distal end 260 thereof. The numerical suffix "4" hereinafter designates corresponding reference characters to those like structural features described above. The enlarged head is provided with an O-ring 486 about the periphery thereof for engaging and perfecting a fluid-tight seal within the central passage 466 to prevent cement contamination within the central passage 466. According to this embodiment, fluidic uncured cement 470 is injected immediately below, or distal, the intermediate collar portion 420. In order to direct the cement 470 toward the proximal end 458, the first seal 424 is provided with at least one, and preferably three, slots 488 for conducting the fluidic cement therepast. The slots 488 are best illustrated in FIG. 10 disposed in equal radial increments about the otherwise frusto-conically shaped first seal 424.

Further to this embodiment, the resilient seal member 440 adjacent the distal end 460 of the intermediate collar portion 420 is formed of a thin fully disk-like material which remains in the femoral canal 436 after implantation of the stem portion 416. Thus, as illustrated in FIG. 11, the resilient seal member 440 is deformed and forced along the femoral canal 436 with the distal tip of the stem 416. Alternatively, however not shown, the resilient seal member 440 can be puncturable or otherwise rupturable, such that as the distal tip of the stem 416 is forced into contact therewith during stem 416 implantation, the resilient seal member 440 punctures to permit movement of the stem portion 416 therethrough.

Figures 12, 13:
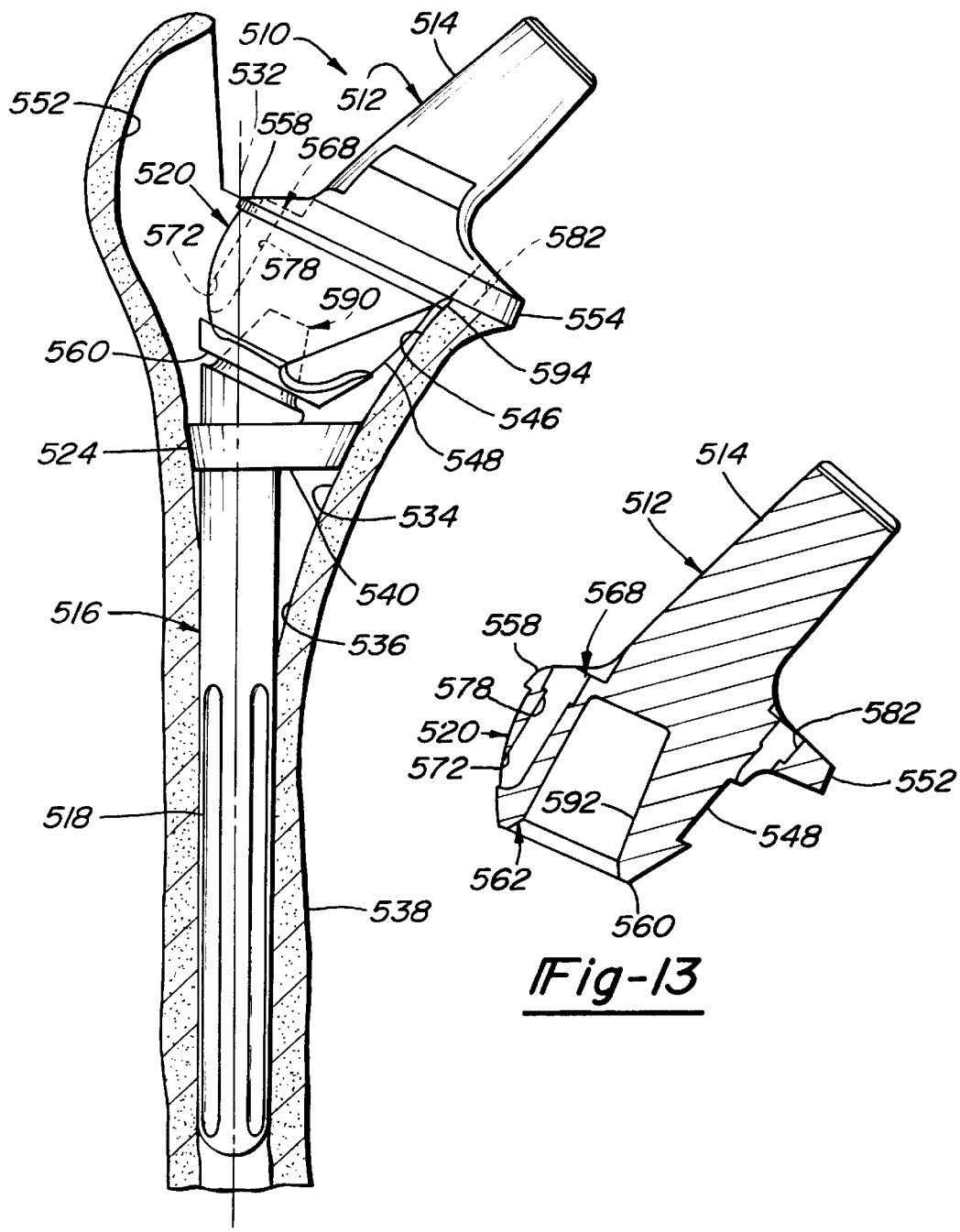
FIG. 12 is an elevational view of still another embodiment of the present invention.
FIG. 13 is a cross-sectional view of the integral neck and intermediate portion of the embodiment shown in FIG. 12.

In FIGS. 12–13, a still further embodiment of the modular prosthesis 510 is shown wherein the neck 512 and intermediate portion 520 are formed integrally with only the stem 516 being detachable. The numerical suffix "5" hereinafter designates corresponding reference characters to those like structural features described above. In this embodiment, the stem 516 is first implanted in the femoral canal 536 as described above. A resilient seal member 540 surrounds a proximal end of the stem 516 for preventing leakage of cement distally into the femoral canal 536.

As referred to above, in this embodiment, the neck 512 is integrally fixed to the intermediate portion 520 so as to form a proximal module. This integral neck 512 and intermediate portion 520 module can be formed in various sizes in order to accurately fit each patient's unique femur. By adapting the prosthesis 510 to each patient's femur, cortical contact in both the coronal and sagittal planes can be optimized and routinely achieved. It is this cortical bone contact that ensures the initial mechanical stability of the prosthesis 510.

As with previous embodiments, the prosthesis 510 includes a disconnection means 562 between the neck 512/intermediate portion 520 module and the stem 516. The disconnection means 562 includes mating frusto-conical fittings to quickly and securely interconnect the two portions and increase intra-operative flexibility while reducing prosthesis 510 part inventory. More specifically, the stem 516 has a proximal end provided with a male taper element 590, The distal end 560 of the intermediate portion 520 is provided with a female receptacle 592 for frictionally engaging the male taper element 590. The inter-locked male taper element 590 and female receptacle 592 are self-locking upon the application of compressive loads during assembly, and in many respects resemble the well-known Morse taper.

A cortical bone engagement means 594 extends from the intermediate portion 520 for engaging the cortical bone 546 upon full implantation. The cortical bone engagement means 594 engages the cortical bone 546 in surface-to-surface engagement and transfers forces from the intermediate portion 520 to the cortical bone 546 in directions normal to the surface-to-surface engagement. The cortical bone engagement means 594 comprises a rim-like flange disposed about the proximal end 558 of the intermediate portion 520 for transferring forces generally radially, albeit somewhat obliquely, of the longitudinal axis 532 of the prosthesis 510. In this manner, loads transferred from the prosthesis 510 generally radially of the longitudinal axis 538 are not borne entirely by the cement surrounding the intermediate portion 520. Instead, the cortical bone engagement means 594 transfers such loads directly and perpendicularly to the cortical bone 546.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A long bone prosthesis (10) including a length defining a longitudinal axis (32) and comprising:

a neck portion (12) for simulating a long bone head;

a stem portion (16) including means (18) for force fit engaging a long bone canal; and an intermediate portion (20) disposed between the neck portion (12) and the stem portion (16); and seal means disposed between the intermediate portion (20) and each of the neck and stem portions (16) for containing cement under pressure adjacent the intermediate portion (20) and preventing leaking of cement therefrom during implantation of the prosthesis (10) by contacting adjacent cortical bone as the stem is press-fit into the long bone canal; the seal means including a circumferential flange between the stem portion (16) and the intermediate portion (20) extending radially outwardly from the longitudinal axis (32) for press-fit engaging the long bone canal (36); the circumferential flange constructed as an integral, one-piece unit with the stem portion (16) or the intermediate portion (20).

2. A long bone prosthesis (10) of claim 1 further including a first passageway (22) extending from the neck portion (12) and through the intermediate portion (20) adjacent the seal means disposed between the intermediate portion (20) and the stem portion (16) allowing for injection of cement through the passageway (21) to an area adjacent the intermediate portion (20) and a second passageway (30) extending between the neck portion (12) and the intermediate portion (20) adjacent to the neck portion (12) allowing for exit of blood and debris during injection of cement through the first passageway (22).

3. A long bone prosthesis (10) including a length defining a longitudinal axis (32), and comprising:
 a neck portion (12) for simulating a long bone head;
 a stem portion (16) including means (18) for force fit engaging a long bone canal; and
 an intermediate portion (20) disposed between the neck portion (12) and the stem portion (16); and
 seal means disposed between the intermediate portion (20) and each of the neck and stem portions (16) for containing cement under pressure adjacent the intermediate portion (20) and preventing leaking of cement therefrom during implantation of the prosthesis (10) by contacting adjacent cortical bone as the stem is press-fit into the long bone canal;
 a first passageway (22) extending from the neck portion (12) and through the intermediate portion (20) adjacent the seal means disposed between the intermediate portion (20) and the stem portion (16) allowing for injection of cement through the passageway (21) to an area adjacent the intermediate portion (20) and a second passageway (30) extending between the neck portion (12) and the intermediate portion (20) adjacent to the neck portion (12) allowing for exit of blood and debris during injection of cement through the first passageway (22);
 the seal means includes a first seal (24) including a circumferential flange between the stem portion (16) and intermediate portions (20) extending radially outwardly from the longitudinal axis (32) for being press-fit at the mouth (34) of the long bone canal (36), the prosthesis including a second seal between the neck portion (12) and intermediate portion (20) extending radially outwardly therefrom for sealing engagement with an inner cortical boundary, the intermediate portion having an outer surface which is substantially conical in shape tapering towards the first seal (24) and recessed radially inwardly relative to each adjacent first and second seal for forming a chamber (52) between the seals when the stem portion (16) is press-fit in the long bone canal (36);
 the circumferential flange constructed as an integral, one-piece unit with the stem portion (16) and the intermediate portion (20).

4. A long bone prosthesis (10) of claim 3 wherein the first seal (24) includes an outer conical surface tapering radially inwardly towards the stem portion (16).

5. A long bone prosthesis (10) of claim 4 further including resilient seal means disposed adjacent said first seal for cooperating with the first seal (24), (124) to perfect a seal between the stem portion (16), (116) and the mouth (34) of the long bone canal 36.

6. A long bone prosthesis (10) of claim 5 wherein the resilient seal means includes a ring-shaped resilient seal member (40) disposed about the stem portion (16) adjacent to the first seal (24).

7. A long bone prosthesis (10) of claim 6 wherein the ring-shaped resilient seal member (40) includes an outer frusto-conical surface.

8. A long bone prosthesis (10) of claim 5 wherein the first seal includes an annular recess (42) extending radially inwardly from the outer surface thereof, the resilient seal means including a ring-shaped resilient seal (44) disposed in the annular recess (42).

9. A long bone prosthesis (10) of claim 3 wherein the intermediate portion (20) includes anti-rotation means (48) extending radially outwardly therefrom along the longitudinal axis (32) and tapering inwardly towards and spaced from the first seal (24) for mating engagement with the cortical bone to prevent relative rotation therebetween.

10. A long bone prosthesis (10) comprising:
 a neck portion (12) for simulating a long bone head;
 a stem portion (16) including means (18) for force fit engaging a long bone canal; and
 an intermediate portion (20) disposed between the neck portion (12) and the stem portion (16);
 seal means disposed between the intermediate portion (20) and each of the neck and stem portions (16) for containing cement under pressure adjacent the intermediate portion (20) and preventing leaking of cement therefrom during implantation of the prosthesis (10) by contacting adjacent cortical bone as the stem is press-fit into the long bone canal;
 a first passageway (22) extending from the neck portion (12) and through the intermediate portion (20) adjacent the seal means disposed between the intermediate portion (20) and the stem portion (16) allowing for injection of cement through the passageway (21) to an area adjacent the intermediate portion (20) and a second passageway (30) extending between the neck portion (12) and the intermediate portion (20) adjacent to the neck portion (12) allowing for exit of blood and debris during injection of cement through the first passageway (22); and
 a length defining a longitudinal axis (32),
 the seal means including a first seal (24) between the stem portion (16) and intermediate portions (20) extending radially outwardly from the longitudinal axis (32) for being press-fit at the mouth (34) of the long bone canal (36),
 a second seal between the neck portion (12) and intermediate portion (20) extending radially outwardly therefrom for sealing engagement with an inner cortical boundary,
 the intermediate portion having an outer surface which is substantially conical in shape tapering towards the first seal (24) and recessed radially inwardly relative to each adjacent first and second seal for forming a chamber (52) between the seals when the stem portion (16) is press-fit in the long bone canal (36);
 the intermediate portion (20) including anti-rotation means (48) extending radially outwardly therefrom along the longitudinal axis (32) and tapering inwardly towards and spaced from the first seal (24) for mating engagement with the cortical bone to prevent relative rotation therebetween;
 the second seal including a collar portion (54) extending radially outwardly from the anti-rotation means (48) adjacent to the neck portion (12), the collar portion (54) defining a forward portion of the second seal opposed to i rear section of the second seal, the rear section of the second seal including a resilient rear seal member (55) mounted on the intermediate portion (20) and extending radially outwardly therefrom for cooperating with the intermediate portion (20) to be fit between the intermediate portion (20) and the inner cortical boundary (46), the rear section of the intermediate portion (20) including a recessed seat portion (56) for seating the resilient rear seal member (55) thereon.

11. A long bone prosthesis (10) comprising:

a neck portion (12) for simulating a long bone head;

a stem portion (16) including means (18) for force fit engaging a long bone canal; and an intermediate portion (20) disposed between the neck portion (12) and the stem portion (16);

seal means disposed between the intermediate portion (20) and each of the neck and stem portions (16) for containing cement under pressure adjacent the intermediate portion (20) and preventing leaking of cement therefrom during implantation of the prosthesis (10) by contacting adjacent cortical bone as the stem is press-fit into the long bone canal;

a first passageway (22) extending from the neck portion (12) and through the intermediate portion (20) adjacent the seal means disposed between the intermediate portion (20) and the stem portion (16) allowing for injection of cement through the passageway (21) to an area adjacent the intermediate portion (20) and a second passageway (30) extending between the neck portion (12) and the intermediate portion (20) adjacent to the neck portion (12) allowing for exit of blood and debris during injection of cement through the first passageway (22); and a length defining a longitudinal axis (32), the seal means including a first seal (24) between the stem portion (16) and intermediate portions (20) extending radially outwardly from the longitudinal axis (32) for being press-fit at the mouth (34) of the long bone canal (36), a second seal between the neck portion (12) and intermediate portion (20) extending radially outwardly therefrom for sealing engagement with an inner cortical boundary, the intermediate portion having an outer surface which is substantially conical in shape tapering towards the first seal (24) and recessed radially inwardly relative to each adjacent first and second seal for forming a chamber (52) between the seals when the stem portion (16) is press-fit in the long bone canal (36);

the intermediate portion (20) including anti-rotation means (48) extending radially outwardly therefrom along the longitudinal axis (32) and tapering inwardly towards and spaced from the first seal (24) for mating engagement with the cortical bone to prevent relative rotation therebetween;

the second seal including a resilient rear seal member (55) mounted on the intermediate portion (20) and extending radially outwardly therefrom for cooperating with the intermediate portion (20) to be fit between the intermediate portion (20) and the inner cortical boundary (46), the rear seal member (55) is an inflatable resilient member for forming a pressure contact between the recessed seat portion (56) and the inner cortical boundary (46) when inflated and for being insertable and removable when deflated.

12. A long bone prosthesis (10) comprising:

a neck portion (12) for simulating a long bone head;

a stem portion (16) including means (18) for force fit engaging a long bone canal; and an intermediate portion (20) disposed between the neck portion (12) and the stem portion (16);

seal means disposed between the intermediate portion (20) and each of the neck and stem portions (16) for containing cement under pressure adjacent the intermediate portion (20) and preventing leaking of cement therefrom during implantation of the prosthesis (10) by contacting adjacent cortical bone as the stem is press-fit into the long bone canal;

a first passageway (22) extending from the neck portion (12) and through the intermediate portion (20) adjacent the seal means disposed between the intermediate portion (20) and the stem portion (16) allowing for injection of cement through the passageway (21) to an area adjacent the intermediate portion (20) and a second passageway (30) extending between the neck portion (12) and the intermediate portion (20) adjacent to the neck portion (12) allowing for exit of blood and debris during injection of cement through the first passageway (22); and a length defining a longitudinal axis (32), the seal means including a first seal (24) between the stem portion (16) and intermediate portions (20) extending radially outwardly from the longitudinal axis (32) for being press-fit at the mouth (34) of the long bone canal (36), a second seal between the neck portion (12) and intermediate portion (20) extending radially outwardly therefrom for sealing engagement with an inner cortical boundary, the intermediate portion having an outer surface which is substantially conical in shape tapering towards the first seal (24) and recessed radially inwardly relative to each adjacent first and second seal for forming a chamber (52) between the seals when the stem portion (16) is press-fit in the long bone canal (36);

the intermediate portion (20) including anti-rotation means (48) extending radially outwardly therefrom along the longitudinal axis (32) and tapering inwardly towards and spaced from the first seal (24) for mating engagement with the cortical bone to prevent relative rotation therebetween;

the second seal including a resilient rear seal member (55) mounted on the intermediate portion (20) and extending radially outwardly therefrom for cooperating with the intermediate portion (20) to be fit between the intermediate portion (20) and the inner cortical boundary (46), the rear seal member (55) is a resilient tubular member for forming a press-fit contact between the recessed seat portion (56) and the inner cortical boundary (46).

* * * * *